United States Patent
Joiner et al.

(10) Patent No.: US 6,475,472 B2
(45) Date of Patent: Nov. 5, 2002

(54) ORAL BLEACHING COMPOSITION

(75) Inventors: Andrew Joiner, Bebington (GB); Philip Christopher Waterfield, Bebington (GB)

(73) Assignee: Unilever Home & Personal Care USA division of Conopco, Inc., Greenwich, CT (US)

( * ) Notice: Subject to any disclaimer, the term of this patent is extended or adjusted under 35 U.S.C. 154(b) by 0 days.

(21) Appl. No.: 10/013,602

(22) Filed: Dec. 11, 2001

(65) Prior Publication Data

US 2002/0122776 A1 Sep. 5, 2002

(51) Int. Cl.⁷ ............... A61K 7/16; A61K 7/20
(52) U.S. Cl. ............... 424/53; 424/49
(58) Field of Search ............... 424/53

(56) References Cited

U.S. PATENT DOCUMENTS

| | | | |
|---|---|---|---|
| 5,188,821 A | | 2/1993 | Gaffar et al. |
| 5,360,568 A | * | 11/1994 | Madison et al. ............ 252/102 |
| 5,360,569 A | * | 11/1994 | Madison et al. ............ 252/102 |
| 5,370,826 A | * | 12/1994 | Madison et al. ............ 252/106 |
| 5,616,335 A | | 4/1997 | Nicolle et al. |
| 5,652,207 A | * | 7/1997 | Ghatua ............ 510/116 |
| 5,693,603 A | * | 12/1997 | Ghatua ............ 510/376 |
| 5,753,599 A | * | 5/1998 | Coope et al. ............ 510/116 |
| 5,760,222 A | * | 6/1998 | Coope ............ 540/545 |
| 5,785,957 A | | 7/1998 | Losee et al. |
| 5,858,949 A | * | 1/1999 | Moschnor ............ 510/314 |
| 5,955,415 A | * | 9/1999 | Gutierrez et al. ............ 510/312 |
| 6,136,297 A | | 10/2000 | Sagel et al. |
| 6,185,448 B1 | * | 12/2000 | Joinor et al. ............ 424/53 |
| 6,350,437 B1 | * | 2/2002 | Pasetti et al. ............ 424/53 |

FOREIGN PATENT DOCUMENTS

| | | |
|---|---|---|
| DE | 39 42 643 | 12/1989 |
| EP | 0 545 594 | 11/1992 |
| EP | 0 895 777 | 7/1998 |
| GB | 2 290 234 | 6/1994 |
| WO | 96/05802 | 2/1996 |
| WO | 00/59461 | 10/2000 |

* cited by examiner

*Primary Examiner*—Shep K. Rose
(74) *Attorney, Agent, or Firm*—Milton L. Honig

(57) ABSTRACT

The present invention relates to oral care compositions with an improved teeth whitening effect. This effect is achieved by inclusion in the oral care compositions of certain organic peroxy acids as teeth whitening/bleaching agents, particularly peroxyamidophthalamides together with hydrogen peroxide.

6 Claims, No Drawings

ORAL BLEACHING COMPOSITION

BACKGROUND OF THE INVENTION

Field of the Invention

The present invention relates to an oral composition with an improved teeth whitening effect. More particularly, it relates to an oral composition with an improved teeth whitening effect comprising a safe and effective amount of certain organic peroxyacids.

WO 96/05802 teaches an oral care composition for whitening teeth. The activity is achieved by inclusion in the oral care compositions of certain organic peroxy acids as teeth whitening/bleaching agents, particularly peroxyamidophthalamides and cationic peroxycarboxylic acids such as N-phthalimido per hexanoic acid and quaternary benzylperoxyacid. A more effective use of peracids in a whitening/bleaching agent for use on teeth would be an advantage.

It is an object of the present invention to provide a more effective bleaching composition than that taught in WO 96/05802.

SUMMARY OF THE INVENTION

We have surprisingly found the use of hydrogen peroxide in conjunction with a peracid provides a more effective oral whitening/bleaching agent over the prior art teachings of WO 96/05802.

The present invention provides an oral tooth cleaning composition which includes:

a peracid that is acceptable for physical contact with the inside of a mammalian mouth, characterised in that the composition comprises hydrogen peroxide in the range from 0.01 to 5.0 % w/w of the composition or source thereof, wherein said source generates hydrogen peroxide in the range from 0.01 to 5.0 % w/w of the composition, characterised in that the peracid is a peroxy amido phthalamide having the following formula:

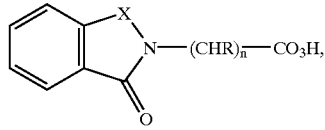

wherein R=hydrogen or $C_1$–$C_4$ alkyl; n=1 to 8; and X=C=O or $SO_2$.

DETAILED DESCRIPTION OF THE INVENTION

The peracid as used obviously need be acceptable to the subject being treated and to regulatory authorities. Such acceptability will be evident to one skilled in the art. The rigours of any regulatory authority will depend upon the jurisdiction and the mammal being treated. Obviously, a higher standard is set for human treatment. The term "acceptable for physical contact" need be construed within the spirit of the teachings as found herein.

The peracid for use in the composition is a peroxy amido phthalamide having the following formula:

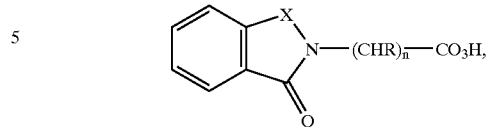

wherein R=hydrogen or $C_1$–$C_4$ alkyl; n=1 to 8; and X=C=O or $SO_2$. A most preferred peracid is N,N-phthaloylaminoperoxycaproic acid (PAP).

Preferably, the peracid is present in the composition at an amount ranging from 0.01 to 5% by weight, more preferably from 0.05 to 4%, especially from 0.1 to 2% and most preferably from 0.5 to 1.5% by weight of the composition.

Certain oral bleaching formulations used under medical supervision may contain up to 35% of hydrogen peroxide. It is within the scope of the present invention for the composition as defined to contain such a high level of hydrogen peroxide in conjunction with a peracid.

Preferably, the peroxide source is present in an amount ranging from 0.05 to 4%, more preferably from 0.1 to 2% by weight of the composition.

The peroxide source is preferably hydrogen peroxide but may also be another source suitable for use in oral care compositions e.g. Carbonide peroxide. The present invention extends to the use of the composition for the whitening/bleaching/cleaning of teeth.

In addition, the present invention also extends to a commercial package comprising a cleaning composition of the present invention, together with instructions for its use.

In contrast to oral use the present invention may also be extended to the cleaning of dentures.

The oral composition according to the invention may also comprise further ingredients which are common in the art, such as:

antimicrobial agents, e.g. Triclosan, chlorhexidine, copper-, zinc- and stannous salts such as zinc citrate, zinc sulphate, zinc glycinate, sodium zinc citrate and stannous pyrophosphate, sanguinarine extract, metronidazole, quaternary ammonium compounds, such as cetylpyridinium chloride; bis-guanides, such as chlorhexidine digluconate, hexetidine, octenidine, alexidine; and halogenated bisphenolic compounds, such as 2,2' methylenebis-(4-chloro-6-bromophenol);

anti-inflammatory agents such as ibuprofen, flurbiprofen, aspirin, indomethacin etc.;

anti-caries agents such as sodium- and stannous fluoride, aminefluorides, sodium monofluorophosphate, sodium trimeta phosphate and casein;

plaque buffers such as urea, calcium lactate, calcium glycerophosphate and strontium polyacrylates;

vitamins such as Vitamins A, C and E;

plant extracts;

desensitising agents, e.g. potassium citrate, potassium chloride, potassium tartrate, potassium bicarbonate, potassium oxalate, potassium nitrate and strontium salts;

anti-calculus agents, e.g. alkali-metal pyrophosphates, hypophosphite-containing polymers, organic phosphonates and phosphocitrates etc.;

biomolecules, e.g. bacteriocins, antibodies, enzymes, etc.;

flavours, e.g. peppermint and spearmint oils;

proteinaceous materials such as collagen; Keratin;

preservatives;

opacifying agents;

colouring agents;

pH-adjusting agents;

sweetening agents;

pharmaceutically acceptable carriers, e.g. starch, sucrose, water or water/alcohol systems etc.;

surfactants, such as anionic, nonionic, cationic and zwitterionic or amphoteric surfactants;

particulate abrasive materials such as silicas, aluminas, calcium carbonates, dicalciumphosphates, calcium pyrophosphates, hydroxyapatites, trimetaphosphates, insoluble hexametaphosphates and so on, including agglomerated particulate abrasive materials, usually in amounts between 3 and 60% by weight of the oral care composition.

humectants such as glycerol, sorbitol, propyleneglycol, xylitol, lactitol etc.;

binders and thickeners such as sodium carboxymethyl-cellulose, xanthan gum, gum arabic etc. as well as synthetic polymers such as polyacrylates and carboxyvinyl polymers such as Carbopol®;

polymeric compounds which can enhance the delivery of active ingredients such as antimicrobial agents can also be included. Examples of such polymers are copolymers of polyvinylmethylether with maleic anhydride and other similar delivery enhancing polymers, e.g. those described in DE-A-3,942,643 (Colgate);

buffers and salts to buffer the pH and ionic strength of the oral care composition; and other optional ingredients that may be included are e.g. bleaching agents such as peroxy compounds e.g. potassium peroxydiphosphate, effervescing systems such as sodium bicarbonate/citric acid systems, colour change systems, and so on.

Liposomes may also be used to improve delivery or stability of active ingredients.

The oral compositions may be in any form common in the art, e.g. toothpaste, gel, mousse, bioadhesive patch/strip, aerosol, gum, lozenge, tooth lacquers, mouthwash, powder, cream, etc. and may also be formulated into systems for use in dual-compartment type dispensers.

Experimental

The bleaching agents were evaluated as follows:

(1) Synthetic hydroxyapatite discs were polished and placed in sterile saliva at 37° C. overnight to form a pellicle.

(2) Discs were stained with tea solution for seven days at 37° C.

(3) Stained discs were immersed in bleaching solutions for desired time.

(4) The change in colour of the discs was measured using a Minolta chromameter CR-300 in L*a*b* mode. Using L* (initial), L* (soiled), and L* (cleaned), the percentage of stain removed was calculated. A negative value indicates a darkening and a positive value indicates a bleaching (whitening) effect.

All formulations used were made up in 0.5 M NaHCO3.

A negative value indicates a darkening and

Table 1 below shows the use of PAP alone in an aqueous 0.5 M NaHCO3 solution together with 0.1 % H2O2.

|  | % Stain Removed 15 mins |
| --- | --- |
| 0.5 M NaHCO3 | −13 |
| 0.5 M NaHCO3/0.1% H2O2 | −11 |
| 0.5 M NaHCO3/1% W/W PAP | 11 |
| 0.5 M NaHCO3/0.1% H2O2/1% W/W M PAP | 16 |

The results show in Table 1, show that the addition of a hydrogen peroxide to the peracid provides a more effective bleaching composition over PAP alone.

Table 2 shows data from a PAP bleaching experiment in which commercial products were used to make formulations.

|  | % Stain Removed | | |
| --- | --- | --- | --- |
|  | 1 min | 5 mins | 10 mins |
| 0.5 M NaHCO3 (control) | −28 | −30 | −31 |
| Eureco ™ HCP-11 (1% w/w PAP) | −4 | 32 | 45 |
| Eureco ™ HCL-17 (1% w/w PAP) | 4 | 47 | 63 |
| 0.1% H2O2 | −30 | −31 | −25 |
| 0.1% H2O2/Eureco ™ HCL-17 (1% w/w PAP) | 7 | 60 | 86 |

Eureco HCP-11 is a commercial formulation containing a PAP/cyclodextrin complex material.

Eureco HCL-17 is a commercial formulation containing an aqueous dispersion of PAP. The aforementioned commercial formulations are available from available from Ausimont: Via S. Pietro, 50/A 1-20021 Bollate, Milano, Italy.

The results shown in Table 2 above show: That the HCL-17 is much more active at bleaching than HCP-11 on an equal w/w basis of PAP. That the presence of 0.1% H2O2 to HCL-17 gives a surprising increase in bleaching effect.

We claim:

1. An oral tooth cleaning composition comprising:

a peracid that is acceptable for physical contact with the inside of a mammalian mouth, the peracid being present in a range from 0.01% to 5.0% w/w of the composition, characterised in that the composition comprises hydrogen peroxide in the range from 0.01 to 5.0 % w/w of the composition or peroxy source thereof, wherein said source generates hydrogen peroxide in the range from 0.01 to 5.0 % w/w of the composition, characterised in that the peracid is a peroxy amido phthalamide having the following formula:

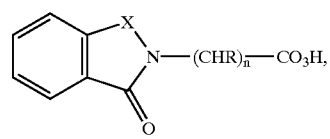

wherein R=hydrogen or $C_1$–$C_4$ alkyl; n=1 to 8; and X=C=O or $SO_2$, said oral composition including an active selected from the group consisting of an anti-inflammatory agent, an anti-caries agent, a vitamin, a desensitising agent which is potassium nitrate, a flavor, a sweetening agent and combinations thereof in functionally effective amounts, wherein said hydrogen peroxide or peroxy source thereof in combination with peracid provides a more effective tooth bleaching or stain removal composition as compared to PAP alone.

2. An oral tooth cleaning composition according to claim 1, wherein the hydrogen peroxide is present in the form of carbamide peroxide.

3. An oral tooth cleaning composition according to claim 1, wherein the peracid is N,N-phthaloylaminoperoxycaproic acid (PAP).

4. An oral tooth cleaning composition according to claim 1, wherein the peracid is in the form of a cyclodextrin complex.

5. An oral tooth cleaning composition according to claim 1, wherein the composition in provided in a format selected from the group consisting of a gel bioadhesive patch/strip, tooth lacquer and a toothpaste.

6. A method of whitening the teeth said method characterised by the following steps:

(i) Applying a composition according to claim 1 to a toothbrush;

(ii) brushing; and, optionally (iii) repeating steps (i) and (ii) if necessary.

* * * * *